(12) United States Patent
Keolsch et al.

(10) Patent No.: US 6,225,103 B1
(45) Date of Patent: *May 1, 2001

(54) CLONING AND CHARACTERIZATION OF NAPSIN

(75) Inventors: Gerald Keolsch, Oklahoma City; Xinli Lin; Jordan Tang, both of Edmond, all of OK (US)

(73) Assignee: Oklahoma Medical Research Foundation, Oklahoma City, OK (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/974,691

(22) Filed: Nov. 20, 1997

Related U.S. Application Data

(60) Provisional application No. 60/031,196, filed on Nov. 20, 1996, and provisional application No. 60/046,126, filed on May 9, 1997.

(51) Int. Cl.[7] .................................................. A61K 38/57
(52) U.S. Cl. ............................ 435/226; 435/212; 435/219
(58) Field of Search .................................... 435/219, 212, 435/226

(56) References Cited

U.S. PATENT DOCUMENTS 5,776,759 * 7/1998 Bandman et al. .................... 435/226

FOREIGN PATENT DOCUMENTS

9510630 * 4/1995 (WO) .

OTHER PUBLICATIONS

Faust et al., PNAS 82: 4910–4914 (Aug. 1985).*
Adams, et al., "Complementary DNA Sequencing: Expressed Sequence Tags and Human Genome Project," *Science* 252: 1651–1656 (1991).
Bock, "Active Site Selective Labeling of Serine Proteases with Spectroscopic Probes Using Thioester Peptide Chloromethyl Ketones: Demonstration of Thrombin Labeling Using $N^\alpha$-[(Acetylthio)acetyl]-D-Phe-Pro-Arg-Ch$_2$Cl," *Biochemistry* 27:6633–6639 (1988).
Brown, et al., "The renin angiotensin system and the regulation of the circulation," *Handbook of Hypertension* vol. 1, Chapter 14, pp. 278–323 (Robertson, ed.) (Elsevier Science Publishers, Amsterdam, 1983).
Clackson, et al. "Making antibody fragments using phage display libraries," *Nature* 352: 624–688 (1991).
Daugherty, et al., "Polymerase chain reaction facilitates the cloning, CDR–grafting, and rapid expression of a murine monoclonal antibody directed against the CD18 component of leukocyte integrins," *Nucl. Acids Res.* 19(9):2471–2476 (1991).

Defize, et al., "Clinical Significance of Pepsinogen A Isozymogens, Serum Pepsinogen A and C Levels, and Serum Gastrin Levels," *Cancer* 59(5):952–958 (1987).
Kim, et al., "Stable propogation of cosmid sized human DNA inserts in an F factor based vector," *Nucl. Acids Res.* 20(5):1083–1085 (1992).
McCafferty, et al. "Phage antibodies: filamentous phage displaying antibody variable domains," *Nature* 348(6301):552–554.
Miki, et al., "The Clinical Applicaiton of the Serum Pepsinogen I and II levels as a Mass Screening Method for Gastric Cancer," *Adv. Exp. Med. Biol.* 362:139–143 (1995).
Miki, et al., "Clinical Application of Serum Pepsinogen I and II Levels for Mass Screening to Detect Gastric Cancer," *Jpn. J. Cancer Res.* 84(10):1086–1090 (1993).
Norman, et al., "Consensus Statement Regarding OKT3–Induced Cytokine–Release Syndrome and Human Antimouse Antibodies," *Transplant Proc.* 25(2)(Suppl. 1):89–93 (1993).
Rochefort, "Biological and Clinical Significance of Cathespin D in Breast Cancer," *Acta Oncologica* 31(2):125–130 (1992).
Samloff, "Peptic Ulcer: The Many Proteinases of Aggression," *Gastroenterology* 96(2)(Part 2 of 2 Parts):586–595 (1989).
Tang, et al., "Structural evidence for gene duplication in the evolution of acid proteases," *Nature* 271(5646):618–621 (1978).
Tang, et al., "Evolution in the Structure and Function of Aspartic Proteases," *J. Cell. Biochem.* 33(1):53–63 (1987).

* cited by examiner

*Primary Examiner*—Jean C. Witz
(74) *Attorney, Agent, or Firm*—Arnall Golden & Gregory, LLP

(57) ABSTRACT

A previously unknown aspartic protease capable of cleavage of proteins by hydrolysis, referred to herein as "napsin", has been cloned from a human liver library. Two cDNA clones have been cloned, sequenced and expressed. These encode isozymes of the protease, referred to as "napsin A" and "napsin B". The gene has also be obtained and partially sequenced. A process for rapid purification of the enzyme using immobilized petpstatin has also been developed, and enzyme isolated from human kidney tissue. Polyclonal antibodies to the enzymes have been made which are also useful for isolation and detection of the enzyme. Similarities to other aspartic proteases, especially cathepsin D, establish the usefulness of the enzyme in diagnostic assays as well as as a protease. Either or both the amount or type of napsin expressed in a particular tissue can be determined using labelled antibodies or nucleotide probes to the napsin.

11 Claims, 18 Drawing Sheets

FIG. 1A

```
  1 ATGTCTCCACCACCGCTgctgcTaccCTtgCTgCTgCTgCTcTGCT   50
    M  S  P  P  P  L  L  L  P  L  L  L  L  L  L 51 GAATGTGGAGCCTGCTGGGGCCACACTGATCCGGATCCCTcTTcGTCAAG  100
    N  V  E  P  A  G  A  T  L  I  R  I  P  L  R  Q  V 101 TCCACCCCTGGACGCAGGACCCTGAACCTACTGAGGGGATGGGGAAAACCA  150
    H  P  G  R  R  T  L  N  L  L  R  G  W  G  K  P 151 GCAGAGCTCCCCAAGTTGGGGCCATCCCCTGGGACAAGCCTGCCTC  200
    A  E  L  P  K  L  G  A  P  S  P  G  D  K  P  A  S 201 GGTACCTCTCTCCAAATTCCTGGATGCCAgTATTTTGGGaAATTGggc  250
    V  P  L  S  K  F  L  D  A  Q  Y  F  G  E  I  G  L 251 tgGGAACGCCTCCACAAAACTTCACTGTTGCCTTTGACACTGGCTCCTCC  300
    G  T  P  P  Q  N  F  T  V  A  F  D  T  G  S  S 301 AATCTCTGGGTCCCCGTTCCAGGAGATGCCACTTCTTCAGTGTGCCCTGCTG  350
    N  L  W  V  P  S  R  R  C  H  F  F  S  V  P  C  W 351 GTTCCACCACCGCTTCAATCCCAATGCCTCCAGCTCCTTCAAGCCCAGTG  400
    F  H  H  R  F  N  P  N  A  S  S  S  F  K  P  S  G 401 GGACCAAGTTTGCCATTCAGTATGGAACTGGGCGGTAGATGGAATCCTG  450
    T  K  F  A  I  Q  Y  G  T  G  R  V  D  G  I  L
```

```
451 AGTgAGGaCAAGCTGACTATtGGTGGAATCaAGGGTGCATCCGTGATTTT   500
     S  E  D  K  L  T  I  G  G  I  K  G  A  S  V  I  F

501 CgggGaAgcTCTGTGGGAATCCAGcctGGTCTTCACTGTTTCCCGCCCCG   550
     G  E  A  L  W  E  S  S  L  V  F  T  V  S  R  P  D 551 ATGGGATATTGGGCCCTCGGTTTTCCCATTCTGTCTGTGGAAGGAgTTCGG  600
     G  I  L  G  F  P  I  L  S  V  E  G  V  R 601 CCCCCGCTGGATGTACTGGTGGAGCAGGGGCTATTGGaTAAGCCTGTCTT   650
     P  P  L  D  V  L  V  E  Q  G  L  L  D  K  P  V  F 651 CTCCTTTTACTTCaACAGGgacCCTGAAgTGGCTGATGGAgGAgAgCTGG   700
     S  F  Y  F  N  R  D  P  E  V  A  D  G  G  E  L  V 701 TCcTgggGGGCTCAgACCCGGCACACTACATCCCACCTTcGTG          750
     L  G  G  S  D  P  A  H  Y  I  P  P  L  T  F  V 751 CCAGTCACAGTCCCCGCCTACTGGCAGATCCACATGGAgCGTGTGAAgGT   800
     P  V  T  V  P  A  Y  W  Q  I  H  M  E  R  V  K  V 801 GGGCTCACGGGCTgActctcTGTGCCCAgGGGCTGTGCCATcCTGGAtA    850
     G  S  R  L  T  L  C  A  Q  G  C  A  A  I  L  D  T 851 CAgGCACACCTGTcATcGTAGgACCCActgAgGAgGAgATCCGGGCCCTGCAT 900
     G  T  P  V  I  V  G  P  T  E  E  I  R  A  L  H
```

FIG. 1B

```
901  GCAGCCATTGGGGGAATCCCCCTTGCTGGGGAgTacATCATCCGGTG  950
      A  A  I  G  G  I  P  L  L  A  G  E  Y  I  R  C

951  CTCagAAATCCCAAAGCTCCCGCAgTcTCCTCACTCCTCATTGGGGGGTcT  1000
      S  E  I  P  K  L  P  A  V  S  L  L  I  G  G  V  W

1001 GGTTTAATCTCCACGgCCCAgGATTACGTCATCCAGTTTGCTCAGGGTGAc  1050
      F  N  L  T  A  Q  D  Y  V  I  Q  F  A  Q  G  D

1051 GTCCGCcTcTGCTTGTCCGGgCCTTGGACATCGCTTCGCCTCC  1100
      V  R  L  C  L  S  G  F  R  A  L  D  I  A  S  P  P

1101 AGTACCTGTGTGGATCCTCGGCGACGTTTTCTTggGGGCGTATGTGACCG  1150
      V  P  V  W  I  L  G  D  V  F  L  G  A  Y  V  T  V

1151 TCTTCGACCCGGGGACATGAAGAGCGGCGCaCgAgTGGGACTGGCCGCGC  1200
      F  D  R  G  D  M  K  S  G  A  R  V  G  L  A  R
                    ─────────────────────────────

1201 GCTCGCCCCTCgCGGAgCGGAGACCTGGGAAGGCGGAGAGCGGCAGGGCA  1250
      A  R  P  R  G  A  D  L  G  R  R  E  T  A  Q  A  Q

1251 GTACCGCGGGTGCCGCCCAGGTGATGCGCATGCGCCACCGGGTAGCCGAGC  1300
      Y  R  G  C  R  P  G  D  A  H  A  H  R  V  A  E  L
```

```
1301 TagcgCTACTCAGTAAAAATCCAATATTTCCATTGAAAAAAAAAAAAAA 1350
        A  L  L  S  K  N  P  I  F  P  L  K  K  K  K  K

1351 AAA 1353
      K
```

```
                    -60        -50        -40        -30        -20
                     .          .          .          .          .
H-Napsin  MSPPPLLLPL LLLLPLLNVE PAGATLIRIP LRQVHPGRRT LNLLRGWGK.
M-KAP     MSP...LLLL LLCLLLGNLE PEEAKLIRVP LQRIHLGHRI LNPLNGWEQ.
H-CathD   .MQPSSLLPL ALCL....LA APASALVRIP LHKFTSIRRT MSEVGGSVED -10         1         10         20         30
                     .          .          .          .          .
H-Napsin  ...PAELPKL GAPSPGDKPA SVP..LSKFL DAQYFGEIGL GTPPQNFTVA
M-KAP     ...LAELSR. .TSTSGGNPS FVP..LSKFM NTQYFGTIGL GTPPQNFTVV
H-CathD   LIAKGPVSKY SQAVPAVTEG PIPEVLKNYM DAQYYGEIGI GTPPQCFTVV 40         50         60         70
                     .          .          .          .
H-Napsin  FDTGSSNLWV PSRRCHFFSV PCWFHHRFNP NASSSFKPSG TKFAIQYGTG
M-KAP     FDTGSSNLWV PSTRCHFFSL ACWFHHRFNP KASSSFRPNG TKFAIQYGTG
H-CathD   FDTGSSNLWV PSIHCKLLDI ACWIHHKYNS DKSSTYVKNG TSFDIHYGSG 80         90        100        110
                     .          .          .          .
H-Napsin  RVDGILSEDK LTI........ .....GGIKGA SVIFGEALWE SSLVFTVSRP
M-KAP     RLSGILSQDN LTI........ .....GGIHDA FVTFGEALWE PSLIFALAHF
H-CathD   SLSGYLSQDT VSVPCQSASS  ASALGGVKVE RQVFGEATKQ PGITFIAAKF
```

F/G. 2A

|            | 120        | 130        | 140        | 150        | 160        |
|------------|------------|------------|------------|------------|------------|
| H-Napsin   | DGILGLGFPI | LSVEGVRPPL | DVLVEQGLLD | KPVFSFYFNR | DPEVADGGEL |
| M-KAP      | DGILGLGFPT | LAVGGVQPPL | DAMVEQGLLE | KPVFSFYLNR | DSEGSDGGEL |
| H-CathD    | DGILGMAYPR | ISVNNVLPFV | DNLMQQKLVD | QNIFSFYLSR | DPDAQPGGEL |

|            | 170        | 180        | 190        | 200        | 210        |
|------------|------------|------------|------------|------------|------------|
| H-Napsin   | VLGGSDPAHY | IPPLTFVPVT | VPAYWQIHME | RVKVGSRLTL | CAQGCAAILD |
| M-KAP      | VLGGSDPAHY | VPPLTFIPVT | IPAYWQVHME | SVKVGTGLSL | CAQGCSAILD |
| H-CathD    | MLGGTDSKYY | KGSLSYLNVT | RKAYWQVHLD | QVEVASGLTL | CKEGCEAIVD |

|            | 220        | 230        | 240        | 250        | 260        |
|------------|------------|------------|------------|------------|------------|
| H-Napsin   | TGTPVIVGPT | EEIRALHAAI | GGIPLLAGEY | IIRCSEIPKL | PAVSLLIGGV |
| M-KAP      | TGTSLITGPS | EEIRALNKAI | GGYPFLNGQY | FIQCSKTPTL | PPVSFHLGGV |
| H-CathD    | TGTSLMVGPV | DEVRELQKAI | GAVPLIQGEY | MIPCEKVSTL | PAITLKLGGK |

FIG. 2B

```
                 270        280        290        300        310
                  .          .          .          .          .
H-Napsin  WFNLTAQDYV IQFAQGDVRL CLSGFRALDI ASPPVPVWIL GDVFLGAYVT
M-KAP     WFNLTGQDYV IQDLQSDVGL CLLGFQALDI PKPAGPLWIL GDVFLGPYVA
H-CathD   GYKLSPEDYT LKVSQAGKTL CLSGFMGMDI PPPSGPLWIL GDVFIGRYYT
                      320  326  330        340        350
                       .    .    .          .          .
H-Napsin  VFDRGDMKSG ARVGLARARP RGADLGRRET AQAQYRGCRP GDAHAHRVAE
M-KAP     VFDRGDKNVG PRVGLARAQS RSTDRAERRT TQAQFFKRRP G.........
H-CathD   VFDRDN.... NRVGFAEAAR L.........
              360        370
               .          .
H-Napsin  LALLSKNPIF PLKKKKK....
M-KAP     ..........
H-CathD   ..........

FIG. 2C
```

```
                                          ATGTCTCCACCACCGCTGC
                                           M  S  P  P  P  L  L
                                                      20
  20  TGCTACCCTTGCTGCTGCTCCTCTGCCTGCTGAATGTGGAGCCTGGGGCCACACTGA
       L  P  L  L  L  L  P  L  L  N  V  E  P  A  G  A  T  L  I
                                                                        30
       TCCGgtatggtgacccca..........ttttcataccctacagGATCCCTCTTC
        R                                              I  P  L  R
                                                                        50
  95  GTCAAGTCCACCCTGGACGCCAGGACCCTGAACCTACTGAGGGGATGGGGAAACCAGCAG
       Q  V  H  P  G  R  R  T  L  N  L  L  R  G  W  G  K  P  A  E
                          40                                  70
       AGCTCCCCAAGTTGGGGGCCCCATCCCCTGGGGACAAGCCTGCCTCGGTACCTCTCTCCA
        L  P  K  L  G  A  P  S  P  G  D  K  P  A  S  V  P  L  S  K
                          60
  215 AATTCCTGGATgtgagtcacagccctacaca......ctctttttttgcctcctcagGCCC
       F  L  D                                                A  Q
                          80                                  90
       AGTATTTTGGGGAAATTGGGCTGGGAACGCCTCCACAAAACTTCACTGTTGCCTTTGACA
       Y  F  G  E  I  G  L  G  T  P  P  Q  N  F  T  V  A  F  D  T

FIG. 3A
```

290 CTGGCTCCTCCAATCTCTGGGTCCCGTCCAGGAGATGCCACTTCTTCAGTGTGCCCTGCT
     G  S  S  N  L  W  V  P  S  R  R  C  H  F  F  S  V  P  C gtgagcttctatgtgtgggaga.....cctctctgacttctgacctagGGTTCCACCACGCT
                                                      W  F  H  H  R  F 365 TCAATCCCAATGCCCTCCAGCTCCTCAAGCCCAGTGGGACCAAGTTTGCCATTCAGTATG
     N  P  N  A  S  S  S  F  K  P  S  G  T  K  F  A  I  Q  Y  G GAACTGGGGCGGGTAGATGGAATCCTGAGTGAGGACAAGCTGACTgtgagtggcctttgac
     G  T  G  R  V  D  G  I  L  S  E  D  K  L  T 469 tcag.....acatctcaatctctacccctagATTGGTGGAATCAAGGGTGCATCCGTGATTT
                                    I  G  G  I  K  G  A  S  V  I  F TCGGGGAAGCTCTGTGGGAATCCAGCCTGGTCTTCACTGTTTCCCGCCCCGATGGGATAT
     G  E  A  L  W  E  S  S  L  V  F  T  V  S  R  P  D  G  I  L

FIG. 3B

```
560  TGGGCCTCGGTTTCCCATTCTGTGTCTGTGGAAGGAGTTCGGCCCCGCTGGATGTACTGG
      G  L  G  F  P  I  L  S  V  E  G  V  R  P  P  L  D  V  L  V
                   190                      200
     TGGAGCAGGGGCTATTGGATAAGCCTGTCTTCTCCTTTTACTTCAACAGgtactgggaag
      E  Q  G  L  L  D  K  P  V  F  S  F  Y  F  N  R
                   210                      220

669  gtgcaccta......gtacactntgccccctgcagGGACCCTGAAGTGGCTGATGGAGGAG
                                          D  P  E  V  A  D  G  G  E
                                                              230
     AGCTGGTCCTGGGGGCTCAGAGCCGGCACACTACATCCCACCCCTCACCTTCGTGCCAG
      L  V  L  G  G  S  D  P  A  H  Y  I  P  P  L  T  F  V  P  V
                         240                      250

755  TCACAGTCCCCCGCCTACTGGCAGATCCACATGGAGCGgtgaggacttggtctcctg.....
      T  V  P  A  Y  W  Q  I  H  M  E  R
                   260                      270
     ..actgcttcctccccctcagTGTGAAGGTGGGCTCACGGCTGACTCTCTGTGCCCAGG
                          V  K  V  G  S  R  L  T  L  C  A  Q  G

FIG. 3C
```

```
                                                    290
830  GCTGTGCTGCCATCCTGGATACAGGCACACCTGTCATCGTAGGACCCACTGAGGAGATCC
     C   A   A   I   L   D   T   G   T   P   V   I   V   G   P   T   E   E   I   R
                                  310
     GGGCCCTGCATGCAGCCATTGGGGGAATCCCCCTTGCTGGGGAGgtgagttccccag
     A   L   H   A   A   I   G   G   I   P   L   L   A   G   E
                                                        320
937  tctct....ttgttcctctcctccaccagTACATCATCCGGTGCTCAGAAATCCCAAAGC
                                  Y   I   I   R   C   S   E   I   P   K   L
                                                        340
     TCCCCGCAGTCTCCACTCCTCATTGGGGGTCTGGTTTAATCTCACGGCCCAGGATTACG
     P   A   V   S   L   L   I   G   G   V   W   F   N   L   T   A   Q   D   Y   V
1028 TCATCCAGgtaggtgtccgtcataatga....gcccgccttgtcgccttgcagTTTGCTC
     I   Q                                                     F   A   Q
                                  360
     AGGGTGACGTCCGCCTCTGCTTGTCCGGCTTCCGGCTTTGGACATCGCTTCGCCTCCAG
     G   D   V   R   L   C   L   S   G   F   R   A   L   D   I   A   S   P   P   V

FIG. 3D
```

```
1103  TACCTGTGTGTGGATCCCTCGGGCCGACGTTTTCTTGGGGCGTATGTGACCGTCTTCGACCGCG
       P  V  W  I  L  G  D  V  F  L  G  A  Y  V  T  V  F  D  R  G
              370                        380

GGGACATGAAGAGCGGCGCACGAGTGGACTGGCGCGCGCCCTCGCGGAGCGGACC
       D  M  K  S  G  A  R  V  G  L  A  R  A  R  P  R  G  A  D  L
              390                        400

1223  TGGGAAGGCGCGAGACCGGCCAGGCCAGTACCCGGGTGCCGCCCAGGTGATGCGCATG
       G  R  R  E  T  A  Q  A  Q  Y  R  G  C  R  P  G  D  A  H  A
              410                        420

CGCACCGGGTAGCCGAGCTAGCTACTCAGTAAAAATCCAATATTTCCATTGAACGAAC
       H  R  V  A  E  L  A  L  L  S  K  N  P  I  F  P  L  .  .  .
              430                        440                  
```

FIG. 3E

```
  1 AATGATCTGTTGTCAACAAGAAACATACTTCACCTACAAATAAAACAGTA   50
 51 AGAGACTGGGTCCTGAAATGCGGGCCCACTTCATATGTGAGGGCAGGTGT  100
101 CTAATCATGTCCTTTCTCCCTTCCCCCAGGCCCTTCACAGATACCTGCTG  150
151 GTCTCTCCCACTTGGCCAAGGAAACANTTGTGGTTAATAAGTCTCAGAAA  200
201 AGTTATGTGAAAGTTAAAAGTAAAACTGACAGCAGCTGAAGGATGGGGGG  250
251 GTGGGAGGTGGTGACGGTGGAGGAGAGCACCCCACCACTGCCACCCAAGT  300
301 AGGGAGTGAGGAGCACCAGGAGCACAGGATGCTACTTCTGCCAACCCTAC  350
351 AAAAATACTCTGCACAAATCTTCAAAAAACATCCTTGTCCCACTGCGTCA  400
401 CCTGCGGACAGATTTCATGTCCTGGTCTCCTTCTAAACCTGGAGGTGGGG  450
451 CATGAACAGGGTGGAGTCACAGGGGAAAGAAAATGAGGCCCCAGGACACC  500
501 TGGGTTCACACCCAGTCCCCAGCGATGTCTCCACCACCGCTGCTGCAAC  550
                                M  S  P  P  P  L  L  Q  P
```

FIG. 4A

551 CCCTGCTGCTGCTGCCTCTGCTGAATGTGGAGCCTTCCGGGCCACA 600
    L   L   L   L   P   L   L   N   V   E   P   S   G   A   T

601 CTGATCCGCATCCCTCTCTTCATCGAGTCCAACCTGACGCAGGATCCTGAA 650
    L   I   R   I   P   L   H   R   V   Q   P   G   R   R   I   L   N

650 CCTACTGAGGGGATGGAGAGAACCAGCAGAGCTCCCAAGTTGGGGGCCC 700
    L   L   R   G   W   R   E   P   A   E   L   P   K   L   G   A   P

701 CATCCCCTGGGACAAGCCCATTTTCGTACCTCTCTGAACTACAGGAT 750
    S   P   G   D   K   P   I   F   V   P   L   S   N   Y   R   D

751 GTGCAGTATTTTGGGGAAATTGGGCTGGGAACGCCTCCACAAAACTTCAC 800
    V   Q   Y   F   G   E   I   G   L   G   T   P   P   Q   N   F   T

801 TGTTGCCTTTGACACTGGCTCCTCCAATCTCTGGGTCCCGTCCAGGAGAT 850
    V   A   F   D   T   G   S   S   N   L   W   V   P   S   R   R   C

851 GCCACTTCTTCAGTGCCCTGCTGGTTACACCACCGATTTGATCCCAAA 900
    H   F   F   S   V   P   C   W   L   H   H   R   F   D   P   K

901 GCCTCTAGCTCCTTCCAGGCCAATGGGACCAAGTTTGCCATTCAATATGG 950
    A   S   S   S   F   Q   A   N   G   T   K   F   A   I   Q   Y   G

FIG. 4B

```
 951 AACTGGGCGGGTAGATGGAATCCTGAGCGAGGACAAGCTGACTATTGGTG 1000
      T  G  R  V  D  G  I  L  S  E  D  K  L  T  I  G  G

1001 GAATCAAGGGTGCATCAGTGATTTTCGGGGAGGCTCTCTGGGAGCCCAGC 1050
      I  K  G  A  S  V  I  F  G  E  A  L  W  E  P  S

1051 CTGGTCTTCGCTTTTGCCCATTTTGATGGGATATTGGGCCTCGGTTTTCC 1100
      L  V  F  A  F  A  H  F  D  G  I  L  G  L  G  F  P

1101 CATTCTGTCTGTGGAAGGAGTTCGGCCCCGATGGATGTACTGGTGGAGC 1150
      I  L  S  V  E  G  V  R  P  P  M  D  V  L  V  E  Q

1151 AGGGGCTATTGGATAAGCCCTGTCTTCTCCTTTTACCTCAACAGGACCCT 1200
      G  L  L  D  K  P  V  F  S  F  Y  L  N  R  D  P

1201 GAAGAGCCTGATGGAGGAGAGCTGGTCCTGGGGCTCGGACCCGGCACA 1250
      E  E  P  D  G  G  E  L  V  L  G  G  S  D  P  A  H

1251 CTACATCCCACCCCTCACCTTCGTGCCAGTCACGGTCCCTGCCTACTGGC 1300
      Y  I  P  P  L  T  F  V  P  V  T  V  P  A  Y  W  Q

1301 AGATCCACATGGAGCGTGTGAAGGTGGGCCCAGGGCTGACTCTCTGTGCC 1350
      I  H  M  E  R  V  K  V  G  P  G  L  T  L  C  A
```

FIG. 4C

1351 AAGGGCTGTGCTGCCATCCTGGATACGGGCACGTCCCTCATCACAGGACC 1400
      K  G  C  A  A  I  L  D  T  G  T  S  L  I  T  G  P

1401 CACTGAGGAGATCCGGGCCCTGCATGCAGCCATTGGGGAATCCCCTTGC 1450
      T  E  E  I  R  A  L  H  A  A  I  G  G  I  P  L  L

1451 TGGCTGGGGAGTACATCATCCTGTGCTCGGAAATCCCAAAGCTCCCCGCA 1500
      A  G  E  Y  I  I  L  C  S  E  I  P  K  L  P  A

1501 GTCTCCTTCCTTCTTGGGGGTCTGGTTTAACCTCACGGCCCATGATTA 1550
      V  S  F  L  L  G  G  V  W  F  N  L  T  A  H  D  Y

1551 CGTCATCCAGACTACTCGAAATGGCGTCCGCCTCTGCTTGTCCGGTTTCC 1600
      V  I  Q  T  T  R  N  G  V  R  L  C  L  S  G  F  Q

1601 AGGCCCTGGATGTCCCGCCTCCGCCAGGGCCCTTCTGGATCCTCGGTGAC 1650
      A  L  D  V  P  P  P  A  G  P  F  W  I  L  G  D

1651 GTCTTCTTGGGGACGTATGTGGCCGTCTTCGACCGCGGGACATGAAGAG 1700
      V  F  L  G  T  Y  V  A  V  F  D  R  G  D  M  K  S

1701 CAGCGCCCGGGTGGGCCTGGCGCGCTCGCACTCGCGGAGCGGACCTCG 1750
      S  A  R  V  G  L  A  R  A  R  T  R  G  A  D  L  G

FIG. 4D

```
1751  GATGGGGAGAGACTGCGCAGGCGCAGTTCCCCGGGTGACGCCCAAGTGAA  1800
       W  G  E  T  A  Q  Q  F  P  G
1801  GCGCATGCGCCAGCGGGTGGTCGCGGAGGTCCTGCTACCCAGTAAAAATCC  1850
1851  ACTATTTCCATTGAAAAAAAAAAAAAAAAAAAAAAAAAAAAAAAAAAAA  1900
1901  AAAAAAAAAA  1910
```

FIG. 4E

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 1353 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens (xi) SEQUENCE DESCRIPTION: SEQ ID NO:1:

```
ATGTCTCCAC CACCGCTGCT GCTACCCTTG CTGCTGCTGC TGCCTCTGCT GAATGTGGAG      60

CCTGCTGGGG CCACACTGAT CCGGATCCCT CTTCGTCAAG TCCACCCTGG ACGCAGGACC    120

CTGAACCTAC TGAGGGGATG GGGAAAACCA GCAGAGCTCC CCAAGTTGGG GGCCCCATCC    180
```

```
CCTGGGGACA AGCCTGCCTC GGTACCTCTC TCCAAATTCC TGGATGCCCA GTATTTTGGG      240

GAAATTGGGC TGGGAACGCC TCCACAAAAC TTCACTGTTG CCTTTGACAC TGGCTCCTCC      300

AATCTCTGGG TCCCGTCCAG GAGATGCCAC TTCTTCAGTG TGCCCTGCTG GTTCCACCAC      360

CGCTTCAATC CCAATGCCTC CAGCTCCTTC AAGCCCAGTG GGACCAAGTT TGCCATTCAG      420

TATGGAACTG GGCGGGTAGA TGGAATCCTG AGTGAGGACA AGCTGACTAT GGTGGAATC       480

AAGGGTGCAT CCGTGATTTT CGGGGAAGCT CTGTGGGAAT CCAGCCTGGT CTTCACTGTT      540

TCCCGCCCCG ATGGGATATT GGGCCTCGGT TTTCCCATTC TGTCTGTGGA AGGAGTTCGG      600

CCCCCGCTGG ATGTACTGGT GGAGCAGGGG CTATTGGATA AGCCTGTCTT CTCCTTTTAC      660

TTCAACAGGG ACCCTGAAGT GGCTGATGGA GGAGAGCTGG TCCTGGGGGG CTCAGACCCG      720

GCACACTACA TCCCACCCCT CACCTTCGTG CCAGTCACAG TCCCCGCCTA CTGGCAGATC      780

CACATGGAGC GTGTGAAGGT GGGCTCACGG CTGACTCTCT GTGCCCAGGG CTGTGCTGCC      840

ATCCTGGATA CAGGCACACC TGTCATCGTA GGACCCACTG AGGAGATCCG GGCCCTGCAT      900

GCAGCCATTG GGGAATCCC CTTGCTGGCT GGGGAGTACA TCATCCGGTG CTCAGAAATC       960

CCAAAGCTCC CCGCAGTCTC ACTCCTCATT GGGGGGGTCT GGTTTAATCT CACGGCCCAG     1020

GATTACGTCA TCCAGTTTGC TCAGGGTGAC GTCCGCCTCT GCTTGTCCGG CTTCCGGGCC     1080

TTGGACATCG CTTCGCCTCC AGTACCTGTG TGGATCCTCG GCGACGTTTT CTTGGGGGCG     1140

TATGTGACCG TCTTCGACCG CGGGGACATG AAGAGCGGCG CACGAGTGGG ACTGGCGCGC     1200

GCTCGCCCTC GCGGAGCGGA CCTGGGAAGG CGCGAGACCG CGCAGGCGCA GTACCGCGGG     1260

TGCCGCCCAG GTGATGCGCA TGCGCACCGG GTAGCCGAGC TAGCGCTACT CAGTAAAAAT     1320

CCAATATTTC CATTGAAAAA AAAAAAAAAA AAA                                 1353
```

(2) INFORMATION FOR SEQ ID NO:2:

(i) SEQUENCE CHARACTERISTICS:
        (A) LENGTH: 451 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:2:

```
Met Ser Pro Pro Leu Leu Pro Leu Leu Leu Leu Pro Leu
1               5                   10                  15

Leu Asn Val Glu Pro Ala Gly Ala Thr Leu Ile Arg Ile Pro Leu Arg
                20                  25                  30

Gln Val His Pro Gly Arg Arg Thr Leu Asn Leu Leu Arg Gly Trp Gly
            35                  40                  45

Lys Pro Ala Glu Leu Pro Lys Leu Gly Ala Pro Ser Pro Gly Asp Lys
        50                  55                  60

Pro Ala Ser Val Pro Leu Ser Lys Phe Leu Asp Ala Gln Tyr Phe Gly
65                  70                  75                  80

Glu Ile Gly Leu Gly Thr Pro Pro Gln Asn Phe Thr Val Ala Phe Asp
                85                  90                  95

Thr Gly Ser Ser Asn Leu Trp Val Pro Ser Arg Arg Cys His Phe Phe
            100                 105                 110

Ser Val Pro Cys Trp Phe His His Arg Phe Asn Pro Asn Ala Ser Ser
```

-continued

```
            115                 120                 125
Ser Phe Lys Pro Ser Gly Thr Lys Phe Ala Ile Gln Tyr Gly Thr Gly
    130                 135                 140

Arg Val Asp Gly Ile Leu Ser Glu Asp Lys Leu Thr Ile Gly Gly Ile
145                 150                 155                 160

Lys Gly Ala Ser Val Ile Phe Gly Glu Ala Leu Trp Glu Ser Ser Leu
                165                 170                 175

Val Phe Thr Val Ser Arg Pro Asp Gly Ile Leu Gly Leu Gly Phe Pro
                180                 185                 190

Ile Leu Ser Val Glu Gly Val Arg Pro Leu Asp Val Leu Val Glu
                195                 200                 205

Gln Gly Leu Leu Asp Lys Pro Val Phe Ser Phe Tyr Phe Asn Arg Asp
    210                 215                 220

Pro Glu Val Ala Asp Gly Gly Glu Leu Val Leu Gly Gly Ser Asp Pro
225                 230                 235                 240

Ala His Tyr Ile Pro Pro Leu Thr Phe Val Pro Val Thr Val Pro Ala
                245                 250                 255

Tyr Trp Gln Ile His Met Glu Arg Val Lys Val Gly Ser Arg Leu Thr
                260                 265                 270

Leu Cys Ala Gln Gly Cys Ala Ala Ile Leu Asp Thr Gly Thr Pro Val
    275                 280                 285

Ile Val Gly Pro Thr Glu Glu Ile Arg Ala Leu His Ala Ala Ile Gly
290                 295                 300

Gly Ile Pro Leu Leu Ala Gly Glu Tyr Ile Ile Arg Cys Ser Glu Ile
305                 310                 315                 320

Pro Lys Leu Pro Ala Val Ser Leu Leu Ile Gly Gly Val Trp Phe Asn
                325                 330                 335

Leu Thr Ala Gln Asp Tyr Val Ile Gln Phe Ala Gln Gly Asp Val Arg
                340                 345                 350

Leu Cys Leu Ser Gly Phe Arg Ala Leu Asp Ile Ala Ser Pro Pro Val
    355                 360                 365

Pro Val Trp Ile Leu Gly Asp Val Phe Leu Gly Ala Tyr Val Thr Val
    370                 375                 380

Phe Asp Arg Gly Asp Met Lys Ser Gly Ala Arg Val Gly Leu Ala Arg
385                 390                 395                 400

Ala Arg Pro Arg Gly Ala Asp Leu Gly Arg Arg Glu Thr Ala Gln Ala
                405                 410                 415

Gln Tyr Arg Gly Cys Arg Pro Gly Asp Ala His Ala His Arg Val Ala
                420                 425                 430

Glu Leu Ala Leu Leu Ser Lys Asn Pro Ile Phe Pro Leu Lys Lys Lys
    435                 440                 445

Lys Lys Lys
    450
```

(2) INFORMATION FOR SEQ ID NO:3:

(i) SEQUENCE CHARACTERISTICS:
        (A) LENGTH: 419 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Ser Pro Leu Leu Leu Leu Leu Leu Cys Leu Leu Leu Gly Asn Leu

```
1               5                   10                  15
Glu Pro Glu Glu Ala Lys Leu Ile Arg Val Pro Leu Gln Arg Ile His
                20                  25                  30
Leu Gly His Arg Ile Leu Asn Pro Leu Asn Gly Trp Glu Gln Leu Ala
                35                  40                  45
Glu Leu Ser Arg Thr Ser Thr Ser Gly Gly Asn Pro Ser Phe Val Pro
 50                  55                  60
Leu Ser Lys Phe Met Asn Thr Gln Tyr Phe Gly Thr Ile Gly Leu Gly
 65                  70                  75                  80
Thr Pro Pro Gln Asn Phe Thr Val Val Phe Asp Thr Gly Ser Ser Asn
                85                  90                  95
Leu Trp Val Pro Ser Thr Arg Cys His Phe Ser Leu Ala Cys Trp
                100                 105                 110
Phe His His Arg Phe Asn Pro Lys Ala Ser Ser Ser Phe Arg Pro Asn
                115                 120                 125
Gly Thr Lys Phe Ala Ile Gln Tyr Gly Thr Gly Arg Leu Ser Gly Ile
    130                 135                 140
Leu Ser Gln Asp Asn Leu Thr Ile Gly Gly Ile His Asp Ala Phe Val
145                 150                 155                 160
Thr Phe Gly Glu Ala Leu Trp Glu Pro Ser Leu Ile Phe Ala Leu Ala
                165                 170                 175
His Phe Asp Gly Ile Leu Gly Leu Gly Phe Pro Thr Leu Ala Val Gly
                180                 185                 190
Gly Val Gln Pro Pro Leu Asp Ala Met Val Glu Gln Gly Leu Leu Glu
                195                 200                 205
Lys Pro Val Phe Ser Phe Tyr Leu Asn Arg Asp Ser Glu Gly Ser Asp
                210                 215                 220
Gly Gly Glu Leu Val Leu Gly Gly Ser Asp Pro Ala His Tyr Val Pro
225                 230                 235                 240
Pro Leu Thr Phe Ile Pro Val Thr Ile Pro Ala Tyr Trp Gln Val His
                245                 250                 255
Met Glu Ser Val Lys Val Gly Thr Gly Leu Ser Leu Cys Ala Gln Gly
                260                 265                 270
Cys Ser Ala Ile Leu Asp Thr Gly Thr Ser Leu Ile Thr Gly Pro Ser
                275                 280                 285
Glu Glu Ile Arg Ala Leu Asn Lys Ala Ile Gly Gly Tyr Pro Phe Leu
                290                 295                 300
Asn Gly Gln Tyr Phe Ile Gln Cys Ser Lys Thr Pro Thr Leu Pro Pro
305                 310                 315                 320
Val Ser Phe His Leu Gly Gly Val Trp Phe Asn Leu Thr Gly Gln Asp
                325                 330                 335
Tyr Val Ile Gln Asp Leu Gln Ser Asp Val Gly Leu Cys Leu Leu Gly
                340                 345                 350
Phe Gln Ala Leu Asp Ile Pro Lys Pro Ala Gly Pro Leu Trp Ile Leu
                355                 360                 365
Gly Asp Val Phe Leu Gly Pro Tyr Val Ala Val Phe Asp Arg Gly Asp
                370                 375                 380
Lys Asn Val Gly Pro Arg Val Gly Leu Ala Arg Ala Gln Ser Arg Ser
385                 390                 395                 400
Thr Asp Arg Ala Glu Arg Arg Thr Thr Gln Ala Gln Phe Phe Lys Arg
                405                 410                 415
Arg Pro Gly
```

(2) INFORMATION FOR SEQ ID NO:4:

(i) SEQUENCE CHARACTERISTICS:
        (A) LENGTH: 412 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:4:

```
Met Gln Pro Ser Ser Leu Leu Pro Leu Ala Leu Cys Leu Leu Ala Ala
1               5                   10                  15

Pro Ala Ser Ala Leu Val Arg Ile Pro Leu His Lys Phe Thr Ser Ile
            20                  25                  30

Arg Arg Thr Met Ser Glu Val Gly Gly Ser Val Glu Asp Leu Ile Ala
            35                  40                  45

Lys Gly Pro Val Ser Lys Tyr Ser Gln Ala Val Pro Ala Val Thr Glu
50                  55                  60

Gly Pro Ile Pro Glu Val Leu Lys Asn Tyr Met Asp Ala Gln Tyr Tyr
65                  70                  75                  80

Gly Glu Ile Gly Ile Gly Thr Pro Pro Gln Cys Phe Thr Val Val Phe
                85                  90                  95

Asp Thr Gly Ser Ser Asn Leu Trp Val Pro Ser Ile His Cys Lys Leu
            100                 105                 110

Leu Asp Ile Ala Cys Trp Ile His His Lys Tyr Asn Ser Asp Lys Ser
            115                 120                 125

Ser Thr Tyr Val Lys Asn Gly Thr Ser Phe Asp Ile His Tyr Gly Ser
130                 135                 140

Gly Ser Leu Ser Gly Tyr Leu Ser Gln Asp Thr Val Ser Val Pro Cys
145                 150                 155                 160

Gln Ser Ala Ser Ser Ala Ser Ala Leu Gly Gly Val Lys Val Glu Arg
                165                 170                 175

Gln Val Phe Gly Glu Ala Thr Lys Gln Pro Gly Ile Thr Phe Ile Ala
            180                 185                 190

Ala Lys Phe Asp Gly Ile Leu Gly Met Ala Tyr Pro Arg Ile Ser Val
            195                 200                 205

Asn Asn Val Leu Pro Val Phe Asp Asn Leu Met Gln Gln Lys Leu Val
            210                 215                 220

Asp Gln Asn Ile Phe Ser Phe Tyr Leu Ser Arg Asp Pro Asp Ala Gln
225                 230                 235                 240

Pro Gly Gly Glu Leu Met Leu Gly Gly Thr Asp Ser Lys Tyr Tyr Lys
                245                 250                 255

Gly Ser Leu Ser Tyr Leu Asn Val Thr Arg Lys Ala Tyr Trp Gln Val
            260                 265                 270

His Leu Asp Gln Val Glu Val Ala Ser Gly Leu Thr Leu Cys Lys Glu
            275                 280                 285

Gly Cys Glu Ala Ile Val Asp Thr Gly Thr Ser Leu Met Val Gly Pro
290                 295                 300

Val Asp Glu Val Arg Glu Leu Gln Lys Ala Ile Gly Ala Val Pro Leu
305                 310                 315                 320

Ile Gln Gly Glu Tyr Met Ile Pro Cys Glu Lys Val Ser Thr Leu Pro
                325                 330                 335
```

```
Ala Ile Thr Leu Lys Leu Gly Gly Lys Gly Tyr Lys Leu Ser Pro Glu
            340                 345                 350

Asp Tyr Thr Leu Lys Val Ser Gln Ala Gly Lys Thr Leu Cys Leu Ser
        355                 360                 365

Gly Phe Met Gly Met Asp Ile Pro Pro Ser Gly Pro Leu Trp Ile
    370                 375                 380

Leu Gly Asp Val Phe Ile Gly Arg Tyr Tyr Thr Val Phe Asp Arg Asp
385                 390                 395                 400

Asn Asn Arg Val Gly Phe Ala Glu Ala Ala Arg Leu
                405                 410

(2) INFORMATION FOR SEQ ID NO:5:

(i) SEQUENCE CHARACTERISTICS:
        (A) LENGTH: 1651 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:5:

ATGTCTCCAC CACCGCTGCT GCTACCCTTG CTGCTGCTGC TGCCTCTGCT GAATGTGGAG      60

CCTGCTGGGG CCACACTGAT CCGGTATGGT GACCCCCATT TTCATACCCT ACAGGATCCC     120

TCTTCGTCAA GTCCACCCTG GACGCAGGAC CCTGAACCTA CTGAGGGGAT GGGGAAAACC     180

AGCAGAGCTC CCCAAGTTGG GGCCCCATC CCCTGGGGAC AAGCCTGCCT CGGTACCTCT      240

CTCCAAATTC CTGGATGTGA GTCACAGCCC TACACACTCT TTTTTTGCCT CCTCAGGCCC     300

AGTATTTTGG GGAAATTGGG CTGGGAACGC TCCACAAAA CTTCACTGTT GCCTTTGACA      360

CTGGCTCCTC CAATCTCTGG GTCCCGTCCA GGAGATGCCA CTTCTTCAGT GTGCCCTGCT     420

GTGAGCTTCT ATGTGGGAGA CCTCTCTGAC TTCTGACCTA GGGTTCCACC ACCGCTTCAA     480

TCCCAATGCC TCCAGCTCCT TCAAGCCCAG TGGGACCAAG TTTGCCATTC AGTATGGAAC     540

TGGGCGGGTA GATGGAATCC TGAGTGAGGA CAAGCTGACT GTGAGTGGCC TTTGACTCAG     600

ACATCTCAAT CTACCCCTAG ATTGGTGGAA TCAAGGGTGC ATCCGTGATT TCGGGGAAG      660

CTCTGTGGGA ATCCAGCCTG GTCTTCACTG TTTCCCGCCC CGATGGGATA TTGGGCCTCG     720

GTTTTCCCAT TCTGTCTGTG GAAGGAGTTC GGCCCCCGCT GGATGTACTG GTGGAGCAGG     780

GGCTATTGGA TAAGCCTGTC TTCTCCTTTT ACTTCAACAG GTACTGGGAA GGTGCACCTA     840

GTACACTNTG CCCCTGCAGG GACCCTGAAG TGGCTGATGG AGGAGAGCTG GTCCTGGGGG     900

GCTCAGACCC GGCACACTAC ATCCCACCCC TCACCTTCGT GCCAGTCACA GTCCCCGCCT     960

ACTGGCAGAT CCACATGGAG CGGTGAGGAC TTGGTCTCCT GACTGCTTCC TTCCCCCTCA    1020

GTGTGAAGGT GGGCTCACGG CTGACTCTCT GTGCCCAGGG CTGTGCTGCC ATCCTGGATA    1080

CAGGCACACC TGTCATCGTA GGACCCACTG AGGAGATCCG GGCCCTGCAT GCAGCCATTG    1140

GGGGAATCCC CTTGCTGGCT GGGGAGGTGA GTTCCCCAGT CTCTTTGTTC CTCTCCTCCA    1200

CCAGTACATC ATCCGGTGCT CAGAAATCCC AAAGCTCCCC GCAGTCTCAC TCCTCATTGG    1260

GGGGGTCTGG TTTAATCTCA CGGCCCAGGA TTACGTCATC CAGGTAGGTG TCCGTCATAA    1320
```

```
TGAGCCCGCC TTGTCGCCTT GCAGTTTGCT CAGGGTGACG TCCGCCTCTG CTTGTCCGGC    1380

TTCCGGGCCT TGGACATCGC TTCGCCTCCA GTACCTGTGT GGATCCTCGG CGACGTTTTC    1440

TTGGGGGCGT ATGTGACCGT CTTCGACCGC GGGGACATGA AGAGCGGCGC ACGAGTGGGA    1500

CTGGCGCGCG CTCGCCCTCG CGGAGCGGAC CTGGGAAGGC GCGAGACCGC GCAGGCGCAG    1560

TACCGCGGGT GCCGCCCAGG TGATGCGCAT GCGCACCGGG TAGCCGAGCT AGCGCTACTC    1620

AGTAAAAATC CAATATTTCC ATTGAACGAA C                                    1651
```

(2) INFORMATION FOR SEQ ID NO:6:

(i) SEQUENCE CHARACTERISTICS:
        (A) LENGTH: 445 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:6:

```
Met Ser Pro Pro Leu Leu Pro Leu Leu Leu Leu Pro Leu
1               5                  10                  15

Leu Asn Val Glu Pro Ala Gly Ala Thr Leu Ile Arg Ile Pro Leu Arg
                20                  25                  30

Gln Val His Pro Gly Arg Arg Thr Leu Asn Leu Leu Arg Gly Trp Gly
                35                  40                  45

Lys Pro Ala Glu Leu Pro Lys Leu Gly Ala Pro Ser Pro Gly Asp Lys
50                  55                  60

Pro Ala Ser Val Pro Leu Ser Lys Phe Leu Asp Ala Gln Tyr Phe Gly
65                  70                  75                  80

Glu Ile Gly Leu Gly Thr Pro Pro Gln Asn Phe Thr Val Ala Phe Asp
                85                  90                  95

Thr Gly Ser Ser Asn Leu Trp Val Pro Ser Arg Arg Cys His Phe Phe
                100                 105                 110

Ser Val Pro Cys Trp Phe His His Arg Phe Asn Pro Asn Ala Ser Ser
                115                 120                 125

Ser Phe Lys Pro Ser Gly Thr Lys Phe Ala Ile Gln Tyr Gly Thr Gly
                130                 135                 140

Arg Val Asp Gly Ile Leu Ser Glu Asp Lys Leu Thr Ile Gly Gly Ile
145                 150                 155                 160

Lys Gly Ala Ser Val Ile Phe Gly Glu Ala Leu Trp Glu Ser Ser Leu
                165                 170                 175

Val Phe Thr Val Ser Arg Pro Asp Gly Ile Leu Gly Leu Gly Phe Pro
                180                 185                 190

Ile Leu Ser Val Glu Gly Val Arg Pro Pro Leu Asp Val Leu Val Glu
                195                 200                 205

Gln Gly Leu Leu Asp Lys Pro Val Phe Ser Phe Tyr Phe Asn Arg Asp
                210                 215                 220

Pro Glu Val Ala Asp Gly Gly Glu Leu Val Leu Gly Gly Ser Asp Pro
225                 230                 235                 240

Ala His Tyr Ile Pro Pro Leu Thr Phe Val Pro Val Thr Val Pro Ala
                245                 250                 255

Tyr Trp Gln Ile His Met Glu Arg Val Lys Val Gly Ser Arg Leu Thr
                260                 265                 270
```

```
Leu Cys Ala Gln Gly Cys Ala Ala Ile Leu Asp Thr Gly Thr Pro Val
        275                 280                 285

Ile Val Gly Pro Thr Glu Glu Ile Arg Ala Leu His Ala Ala Ile Gly
    290                 295                 300

Gly Ile Pro Leu Leu Ala Gly Glu Tyr Ile Ile Arg Cys Ser Glu Ile
305                 310                 315                 320

Pro Lys Leu Pro Ala Val Ser Leu Leu Ile Gly Val Trp Phe Asn
                325                 330                 335

Leu Thr Ala Gln Asp Tyr Val Ile Gln Phe Ala Gln Gly Asp Val Arg
            340                 345                 350

Leu Cys Leu Ser Gly Phe Arg Ala Leu Asp Ile Ala Ser Pro Pro Val
        355                 360                 365

Pro Val Trp Ile Leu Gly Asp Val Phe Leu Gly Ala Tyr Val Thr Val
    370                 375                 380

Phe Asp Arg Gly Asp Met Lys Ser Gly Ala Arg Val Gly Leu Ala Arg
385                 390                 395                 400

Ala Arg Pro Arg Gly Ala Asp Leu Gly Arg Arg Glu Thr Ala Gln Ala
                405                 410                 415

Gln Tyr Arg Gly Cys Arg Pro Gly Asp Ala His Ala His Arg Val Ala
            420                 425                 430

Glu Leu Ala Leu Leu Ser Lys Asn Pro Ile Phe Pro Leu
        435                 440                 445

(2) INFORMATION FOR SEQ ID NO:7:

(i) SEQUENCE CHARACTERISTICS:
        (A) LENGTH: 1910 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:7:

AATGATCTGT TGTCAACAAG AAACATACTT CACCTACAAA TAAAACAGTA AGAGACTGGG      60

TCCTGAAATG CGGGCCCACT TCATATGTGA GGGCAGGTGT CTAATCATGT CCTTTCTCCC     120

TTCCCCCAGG CCCTTCACAG ATACCTGCTG GTCTCTCCCA CTTGGCCAAG GAAACANTTG     180

TGGTTAATAA GTCTCAGAAA AGTTATGTGA AAGTTAAAAG TAAAACTGAC AGCAGCTGAA     240

GGATGGGGGG GTGGGAGGTG GTGACGGTGG AGGAGACCCC ACCACCACTG CCACCCAAGT     300

AGGGAGTGAG GAGCACCAGG AGCACAGGAT GCTACTTCTG CCAACCCTAC AAAAATACTC     360

TGCACAAATC TTCAAAAAAC ATCCTTGTCC CACTGCGTCA CCTGCGGACA GATTTCATGT     420

CCTGGTCTCC TTCTAAACCT GGAGGTGGGG CATGAACAGG GTGGAGTCAC AGGGGAAAGA     480

AAATGAGGCC CCAGGACACC TGGGTTCACA CCCAGGTCCC CAGCGATGTC TCCACCACCG     540

CTGCTGCAAC CCCTGCTGCT GCTGCTGCCT CTGCTGAATG TGGAGCCTTC CGGGGCCACA     600

CTGATCCGCA TCCCTCTTCA TCGAGTCCAA CCTGGACGCA GGATCCTGAA CCTACTGAGG     660

GGATGGAGAG AACCAGCAGA GCTCCCCAAG TTGGGGCCCC CATCCCCTGG GGACAAGCCC     720

ATTTTCGTAC CTCTCTCGAA CTACAGGGAT GTGCAGTATT TTGGGGAAAT TGGGCTGGGA     780
```

```
ACGCCTCCAC AAAACTTCAC TGTTGCCTTT GACACTGGCT CCTCCAATCT CTGGGTCCCG      840

TCCAGGAGAT GCCACTTCTT CAGTGTGCCC TGCTGGTTAC ACCACCGATT TGATCCCAAA      900

GCCTCTAGCT CCTTCCAGGC CAATGGGACC AAGTTTGCCA TTCAATATGG AACTGGGCGG      960

GTAGATGGAA TCCTGAGCGA GGACAAGCTG ACTATTGGTG GAATCAAGGG TGCATCAGTG     1020

ATTTTCGGGG AGGCTCTCTG GGAGCCCAGC CTGGTCTTCG CTTTTGCCCA TTTTGATGGG     1080

ATATTGGGCC TCGGTTTTCC CATTCTGTCT GTGGAAGGAG TTCGGCCCCC GATGGATGTA     1140

CTGGTGGAGC AGGGGCTATT GGATAAGCCT GTCTTCTCCT TTTACCTCAA CAGGGACCCT     1200

GAAGAGCCTG ATGGAGGAGA GCTGGTCCTG GGGGGCTCGG ACCCGGCACA CTACATCCCA     1260

CCCCTCACCT TCGTGCCAGT CACGGTCCCT GCCTACTGGC AGATCCACAT GGAGCGTGTG     1320

AAGGTGGGCC CAGGGCTGAC TCTCTGTGCC AAGGGCTGTG CTGCCATCCT GGATACGGGC     1380

ACGTCCCTCA TCACAGGACC CACTGAGGAG ATCCGGGCCC TGCATGCAGC CATTGGGGGA     1440

ATCCCCTTGC TGGCTGGGGA GTACATCATC CTGTGCTCGG AAATCCCAAA GCTCCCCGCA     1500

GTCTCCTTCC TTCTTGGGGG GGTCTGGTTT AACCTCACGG CCCATGATTA CGTCATCCAG     1560

ACTACTCGAA ATGGCGTCCG CCTCTGCTTG TCCGGTTTCC AGGCCCTGGA TGTCCCTCCG     1620

CCTGCAGGGC CCTTCTGGAT CCTCGGTGAC GTCTTCTTGG GGACGTATGT GGCCGTCTTC     1680

GACCGCGGGG ACATGAAGAG CAGCGCCCGG GTGGGCCTGG CGCGCGCTCG CACTCGCGGA     1740

GCGGACCTCG GATGGGGAGA GACTGCGCAG GCGCAGTTCC CCGGGTGACG CCCAAGTGAA     1800

GCGCATGCGC AGCGGGTGGT CGCGGAGGTC CTGCTACCCA GTAAAAATCC ACTATTTCCA     1860

TTGAAAAAAA AAAAAAAAAA AAAAAAAAAA AAAAAAAAAA AAAAAAAAAA                1910

(2) INFORMATION FOR SEQ ID NO:8:

(i) SEQUENCE CHARACTERISTICS:
        (A) LENGTH: 420 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:8:

Met Ser Pro Pro Pro Leu Leu Gln Pro Leu Leu Leu Leu Pro Leu
1               5                  10                  15

Leu Asn Val Glu Pro Ser Gly Ala Thr Leu Ile Arg Ile Pro Leu His
                20                  25                  30

Arg Val Gln Pro Gly Arg Arg Ile Leu Asn Leu Leu Arg Gly Trp Arg
            35                  40                  45

Glu Pro Ala Glu Leu Pro Lys Leu Gly Ala Pro Ser Pro Gly Asp Lys
        50                  55                  60

Pro Ile Phe Val Pro Leu Ser Asn Tyr Arg Asp Val Gln Tyr Phe Gly
65                  70                  75                  80

Glu Ile Gly Leu Gly Thr Pro Pro Gln Asn Phe Thr Val Ala Phe Asp
                85                  90                  95

Thr Gly Ser Ser Asn Leu Trp Val Pro Ser Arg Cys His Phe Phe
            100                 105                 110

Ser Val Pro Cys Trp Leu His His Arg Phe Asp Pro Lys Ala Ser Ser
        115                 120                 125

Ser Phe Gln Ala Asn Gly Thr Lys Phe Ala Ile Gln Tyr Gly Thr Gly
```

```
                    130                 135                 140
Arg Val Asp Gly Ile Leu Ser Glu Asp Lys Leu Thr Ile Gly Gly Ile
145                 150                 155                 160

Lys Gly Ala Ser Val Ile Phe Gly Glu Ala Leu Trp Glu Pro Ser Leu
                    165                 170                 175

Val Phe Ala Phe Ala His Phe Asp Gly Ile Leu Gly Leu Gly Phe Pro
                    180                 185                 190

Ile Leu Ser Val Glu Gly Val Arg Pro Pro Met Asp Val Leu Val Glu
                    195                 200                 205

Gln Gly Leu Leu Asp Lys Pro Val Phe Ser Phe Tyr Leu Asn Arg Asp
                    210                 215                 220

Pro Glu Glu Pro Asp Gly Gly Glu Leu Val Leu Gly Gly Ser Asp Pro
225                 230                 235                 240

Ala His Tyr Ile Pro Pro Leu Thr Phe Val Pro Val Thr Val Pro Ala
                    245                 250                 255

Tyr Trp Gln Ile His Met Glu Arg Val Lys Val Gly Pro Gly Leu Thr
                    260                 265                 270

Leu Cys Ala Lys Gly Cys Ala Ala Ile Leu Asp Thr Gly Thr Ser Leu
                    275                 280                 285

Ile Thr Gly Pro Thr Glu Glu Ile Arg Ala Leu His Ala Ala Ile Gly
                    290                 295                 300

Gly Ile Pro Leu Leu Ala Gly Glu Tyr Ile Ile Leu Cys Ser Glu Ile
305                 310                 315                 320

Pro Lys Leu Pro Ala Val Ser Phe Leu Leu Gly Gly Val Trp Phe Asn
                    325                 330                 335

Leu Thr Ala His Asp Tyr Val Ile Gln Thr Thr Arg Asn Gly Val Arg
                    340                 345                 350

Leu Cys Leu Ser Gly Phe Gln Ala Leu Asp Val Pro Pro Pro Ala Gly
                    355                 360                 365

Pro Phe Trp Ile Leu Gly Asp Val Phe Leu Gly Thr Tyr Val Ala Val
                    370                 375                 380

Phe Asp Arg Gly Asp Met Lys Ser Ser Ala Arg Val Gly Leu Ala Arg
385                 390                 395                 400

Ala Arg Thr Arg Gly Ala Asp Leu Gly Trp Gly Glu Thr Ala Gln Ala
                    405                 410                 415

Gln Phe Pro Gly
            420

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:9:

AGGGCACACT GAAGAAGTGG CATCTCC                                          27

(2) INFORMATION FOR SEQ ID NO:10:

(i) SEQUENCE CHARACTERISTICS:
        (A) LENGTH: 27 base pairs
        (B) TYPE: nucleic acid
```

```
            (C) STRANDEDNESS: single
            (D) TOPOLOGY: linear (ii) MOLECULE TYPE: DNA (iii) HYPOTHETICAL: NO (xi) SEQUENCE DESCRIPTION: SEQ ID NO:10:

CTTTTGAGCA AGTTCAGCCT GGTTAAG                                               27

(2) INFORMATION FOR SEQ ID NO:11:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (iii) HYPOTHETICAL: NO (xi) SEQUENCE DESCRIPTION: SEQ ID NO:11:

AAGCTTATGT CTCCACCACC GCTGCTGCTA CCCTTGCTGC                                 40

(2) INFORMATION FOR SEQ ID NO:12:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (iii) HYPOTHETICAL: NO (xi) SEQUENCE DESCRIPTION: SEQ ID NO:12:

AAGCTTTTAT TTTTTTTTTT TTTTTTTCAA TGGAAATATT GG                              42

(2) INFORMATION FOR SEQ ID NO:13:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (iii) HYPOTHETICAL: NO (xi) SEQUENCE DESCRIPTION: SEQ ID NO:13:

GAGGGCGAGC GCGCGCCAGT CCCACTCGTG CGCCGCTCTT CATGTCCCCG                      50

(2) INFORMATION FOR SEQ ID NO:14:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (iii) HYPOTHETICAL: NO (xi) SEQUENCE DESCRIPTION: SEQ ID NO:14:

CCATCCCCTC AGTAGGTTCA GGGTCCTGCG TCCAGGGTGG ACTTGACGAA                      50
```

CLONING AND CHARACTERIZATION OF NAPSIN

This application claims the benefit of Provisional Application No. 60/031,196, filed Nov. 20, 1996 and the benifit of Provisional Application No. 60/046,126, filed May 9, 1997.

BACKGROUND OF THE INVENTION

The present invention relates to a previously unknown aspartic protease present in human liver, isolated by cloning of a gene from a human liver cDNA library.

This application claims priority to provisional patent application No. 60/031,196 entitled "Napsin, An Aspartic Protease Present in Human Liver" filed Nov. 20, 1996, by Jordan J. N. Tang, Xinli Lin, and Gerald Koelsch, and provisional patent application No. 60/046,126 entitled "Cloning and Gene Structure of Human Napsin" filed May 9, 1997, by by Jordan J. N. Tang, Xinli Lin, and Gerald Koelsch.

Members of the aspartic protease family are characterized by the presence of catalytic aspartic acid residues in their active center. There are five aspartic proteases known to be present in human body. Pepsin and gastricsin are secreted into the stomach for food digestion. Gastricsin is also present in the seminal plasma. Cathepsin D and cathepsin E are present intracellularly to carry out protein catabolism. Renin, which is present in the plasma, is the key enzyme regulating the angiotensin system and ultimately the blood pressure.

Eukaryotic, including human, aspartic proteases are homologous in protein and gene sequences, but have different amino acid and nucleotide sequences. The cDNA and genes of all five human aspartic proteases have been cloned and sequenced. They are synthesized as a single chain zymogen of about 380 residues, which are either secreted or directed to intracellular vacuoles. Upon activation by a self-catalyzed process (except prorenin), an N-terminal pro segment of about 45-residues is cleaved off to produce mature enzymes (Tang and Wong, *J. Cell. Biochem.* 33, 53–63 (1987)). In some cases, for example, with cathepsin D and renin, mature proteases are further cut into two chains. The three-dimensional structures of the aspartic proteases are very similar. Each enzyme contains two internally homologous lobes (Tang et al., *Nature* 271, 618–621 (1978)). The active-site cleft, which can accommodate eight substrate residues, and two catalytic aspartic acids, are located between the lobes.

These proteases have distinct and important physiological roles. In addition to their importance in physiological functions, these enzymes are also associated with pathological states. For example, human pepsin and gastricsin are diagnostic indicators for stomach ulcer and cancer (Samloff, *Gastroenterology* 96, 586–595 (1989); Miki et al., *Jpn. J. Cancer Res.* 84, 1086–1090 (1993)). Cathepsin D is located in the lysosome. Its main function is the catabolism of tissue proteins. Recent evidence from mice without a functional cathepsin D gene, however, indicates that this enzyme plays a role in the development of intestine in newborn animals. Cathepsin D is also associated with human breast cancer metastasis (Rochefort, *Acta Oncologica* 31, 125–130 (1992)). Cathepsin E is located in the endoplasmic reticulum of some cells, such as erythrocyte and stomach mucosa cells. It has been applied in the processing of antigens in the immune cells.

Human aspartic proteases have important medical uses. The levels of the proenzymes of human pepsinogen and progastricsin present in the bloodstream and the ratio between the two levels is used in the diagnostic screening of human stomach cancer (Defize, et al., *Cancer* 59, 952–958 (1987); Miki, et al., *Jpn. J. Cancer Res.* 84, 1086–1090 (1993)) and ulcer (Miki, et al., *Adv. Exp. Med. Biol.* 362, 139–143 (1995)). The secretion of procathepsin D is elevated in breast cancer tissue. Thus, the level of procathepsin D in breast cancer is used for clinical prognosis (Rochefort, *Acta Oncologica* 31, 125–130 (1992)). The analysis of renin in the diagnosis of hypertension is a routine clinical procedure (Brown et al., *Handbook of Hypertension* 1, 278–323 Robertson, editor (Elsevier Science Publishers, Amsterdam, 1983).

These examples establish that human aspartic proteases are related to human diseases and additional, previously unidentified aspartic proteases, are likely to have clinical applications.

It is therefore an object of the present invention to provide a previously unidentified aspartic protease.

It is a further object of the present invention to characterize and to clone the aspartic protease.

It is still another object of the present invention to identify the tissues in which the aspartic protease is expressed and applications in clinical chemistry and diagnostics.

SUMMARY OF THE INVENTION

A previously unknown aspartic protease capable of cleavage of proteins by hydrolysis, referred to herein as "napsin", has been cloned from a human liver library. Two cDNA clones have been cloned, sequenced and expressed. These encode isozymes of the protease, referred to as "napsin A" and "napsin B". One clone is unusual in that it does not include a stop codon but can be used to express protein. The gene has also be obtained and partially sequenced. A process for rapid purification of the enzyme using immobilized petpstatin has also been developed, and enzyme isolated from human kidney tissue. Polyclonal antibodies to the enzymes have been made which are also useful for isolation and detection of the enzyme.

Similarities to other aspartic proteases, especially cathepsin D, establish the usefulness of the enzyme in diagnostic assays as well as as a protease. Either or both the amount or type of napsin expressed in a particular tissue can be determined using labelled antibodies or nucleotide probes to the napsin.

BRIEF DESCRIPTION OF THE DRAWINGS

FIG. 1A–1D are the cDNA (SEQ ID No. 1) and putative amino acid sequence (SEQ ID No. 2) of human Napsin A. Characteristic active site elements (DTG) and Tyr75 are underlined. The RGD integrin binding motif is also underlined. Lysines at the carboxy terminus correspond to the poly-A region.

FIG. 2A–C are a comparison of the human napsin A amino acid sequence (SEQ ID No. 2) with the amino acid sequences of mouse aspartic protease-like protein (Mori, et al., 1997, SEQ ID No. 3) and human cathepsin D ("cath D"SEQ ID No.4 ).

FIG. 3A–3E are the genomic DNA (SEQ ID No. 5) of human Napsin A. Introns are indicated in lower-case letter, exons in upper case. Putative amino acid sequence (SEQ ID No. 6.) indicates position of intro-exon junctions.

FIG. 4A–4E are the cDNA (SEQ ID No. 7) and putative amino acid sequence (SEQ ID No. 8) of human Napsin B. Characteristic active site elements (DTG) and Tyr75 are underlined. The RGD integrin binding motif is also underlined. Lysines at the carboxy terminus correspond to the poly-A region.

DETAILED DESCRIPTION OF THE INVENTION

Figure 2D:
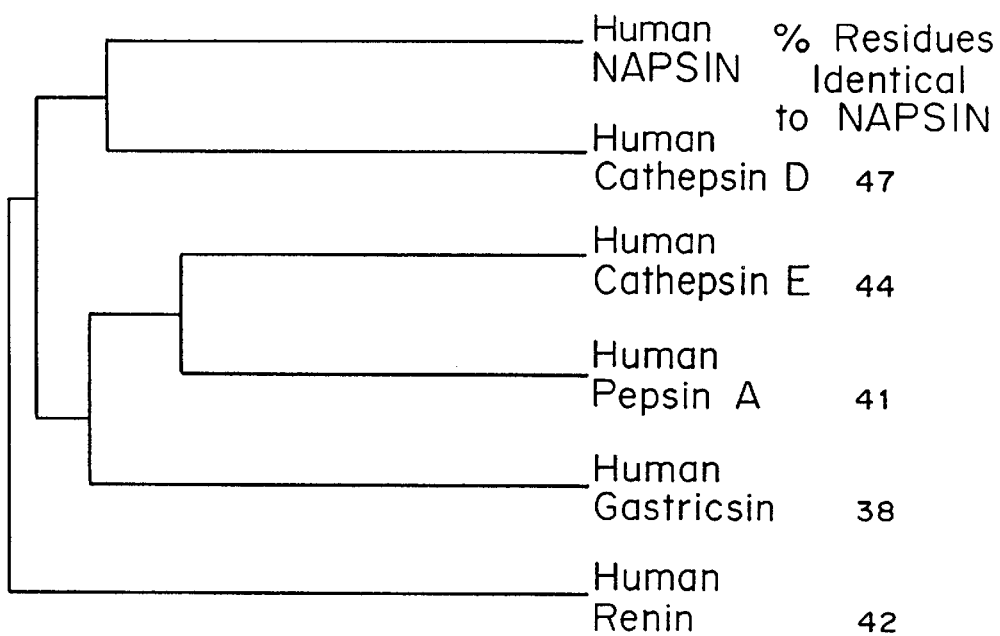
FIG. 2D is a schematic or dendrogram presentation of sequence relatedness between napsin and other human aspartic proteases.

I. Cloning and Expression of Napsin Isoforms.
A. Human Napsin A.
1. Cloning of cDNA encoding Napsin A.

Clones identified by a homology search of the human cDNA sequence database of the Institute for Genome Research (Adams et al., Science 252, 1651–1656 (1991), reported to encode portions of cathepsin D, were obtained from the American Type Culture Collection, Rockville, Md. These are referred to as ATCC clone number 559204, 540096, 346769, 351669, and 314203; Genbank numbers W19120, N45144, R18106, R11458, and T54068, respectively. Analysis of the sequences indicated these did not encode cathepsin D, and were not full length cDNAs. Primers were designed and used with PCR to obtain additional clones, using a human liver cDNA library as the template. The clones that were obtained include regions not present in the ATCC clones.

Since these clones together provided only about 600 bp of the cDNA, a longer cDNA clone was sought using 5' RACE PCR (polymerase chain reaction), in which DNA from two separate human liver cDNA libraries cloned into λgt10 was used as template and the primers were based on the near 5'-end sequence (AGGGCACACTGAAGAAGTGGCATCTCC) (SEQ ID No. 9) and the sequence of the λgt10 vector upstream from the insert in the forward direction (CTTTTGAGCAAGTTCAGCCTGGTTAAG) (SEQ ID No. 10). Two clones, pHL-1 (154 bp) and pHL-2 (288 bp) were obtained, one (pHL-2) of which extended the 5'-end sequence into the leader peptide region (FIGS. 1A–1D).

Human napsin A cDNA sequence lacks a stop codon from all clones obtained, yet all features otherwise indicate a functional aspartic protease, including intact active site elements, a conserved Tyr75 (pepsin numbering), and a pro-peptide of approximately 40 amino acids. Different from pepsin, the characteristic aspartic protease, napsin A contains a C-terminal extension, abundance of proline residues, and an RGD motif (integrin-binding motif) near the surface of the 3-D structure of napsin as judged by homologous crystal structures of mammalian aspartic proteases (i.e., pepsin and cathepsin D).

Several related cDNA clones of napsin were obtained by screening of a human liver cDNA library and the nucleotide sequences determined. These clones represent different parts of napsin messenger RNA. Spliced together, the nucleotide sequence encoding napsin A (SEQ ID No. 1) having the deduced amino acid sequence (SEQ ID No. 2) is shown in FIGS. 1A–1D.

2. Expression of Recombinant Napsin A

The cDNA of napsin A, including the leader peptide and the 3' untranslated region and a stretch of polyadenine, was PCR amplified with primers PLHNAP-FWD (SEQ ID No. 11) (5'-AAGCTATGTCTCCACCACCGCTGCTGCTAC-CCTTGCTGC) and PLHNAP-REV (SEQ ID No. 12) (5'-AAGCTTTATTTTTTTTTTTTTTTTTTCAATGGAAAT-ATTGG) and cloned into the HindIII site of vector pLNCX for expression from the CMV promoter (Dusty Miller). Isolated plasmid was transformed into human kidney 293 cells (ATCC). Cells were recovered (8–120 mg) and lysed with 50 mM NaOAc, 20 mM zwittergent, pH 3.5 (NAZ buffer) with vortexing. Lysate was incubated on ice for 1 hour. The supernatant from centrifugation at 14,000 xg was employed directly for detection of expressed Napsin A by addition of a 40 μl aliquot of pepstatin-A-agarose (Sigma). The sample was rotated in a 50 ml conical tube at 4° C. for 1 week. The matrix was settled and washed twice with 20 ml of NAZ buffer, and three times with 20 mM Tris HCl, 0.5 M KCl, pH 8.2 (TK buffer). Final washes were performed with 20 mM Tris HCl, 50 mM NaCl, and 20 mM zwittergent, pH 9.5. The settled pepstatin-A-agarose (approximately 40 μl) was mixed with 40 μl of SDS-β-mercaptoethanol sample buffer (NOVEX) and heated to 70° C. for 10 minutes. Aliquots were applied to 10% Tricine SDS-PAGE (NOVEX) and transblotted to PVDF membranes using a Tris-Tricine buffer system. Membranes were either stained with amido black or blocked with 5% skim milk solution for immunochemical detection. Sections of membrane stained with amido black were excised and washed in sterile $H_2O$ for amino-terminal sequence analysis in an automated Protein Sequencer.

3. Cloning of Genomic DNA.

Genomic clones of human napsin were obtained by screening of a human genomic DNA library, cloned into bacterial artificial chromosomes (pBELO-BAC11) (Kim et al., Nucl. Acids Res. 20, 1083–1085 (1992)). The source of genomic DNA for the library was from 978SK and human sperm cell lines, and contained over 140,000 clones. Synthetic oligonucleotide probes were labelled with $^{32}P$:

for primary screen Nap-3' (GAGGGCGAGCGCGCGCCAGTCCCACTCGTG-CGCCGCTCTTCATGTC CCCG) (SEQ ID No. 13), and for secondary screening Nap-5' (CCATCCCCTCAGTAGGTTCAGGGTCCTGCGT-CCAGGGTGGACTTGA CGAA) (SEQ ID No. 14).

The screening was carried out at Research Genetics, Huntsville, Alabama. Two independent clones were isolated, both approximately 30 kbp in length, and were cut with restriction enzyme and analyzed by pulse-field agarose gel electrophoresis. Fragments of interest were identified by Southern blotting, subcloned into pBlue, and sequenced. The genomic DNA of human Napsin A is shown in FIGS. 3A–3E.

Figure 3F:
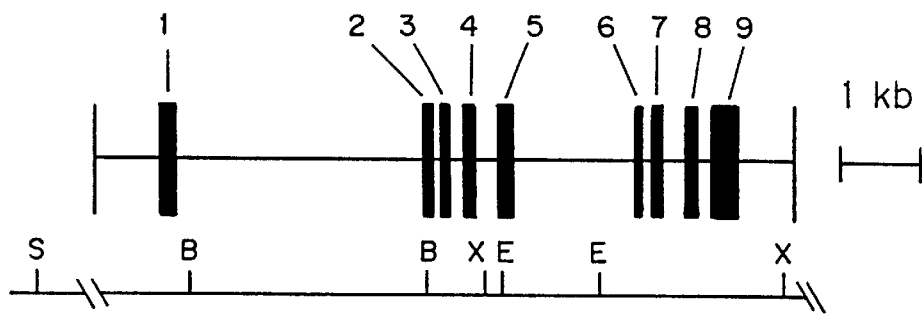
FIG. 3F is a schematic presentation of the human napsin A. The exons are shown as vertical bars with the numbering above. The double-headed arrows represent the areas where sequence was determined. The letters are positions of restriction sites where X is XhoI, B is BamHI, and E is EcoRI.

The human napsin A gene is encoded in 9 exons (FIG. 3F). The exon/intron junctions are clearly defined by both the cDNA sequence and the junction motifs. The human napsin A coding region contains an open reading frame starting from the initiation codon ATG (nucleotide 1 in FIGS. 1A–1D) for about 1.2 kb to a polyA stretch in the cDNA sequences. As in the cDNA sequence of napsin A, the genomic exon sequence of napsin A do not contain an in-frame stop codon in the entire coding region before the polyA stretch. The absence of a stop codon in napsin A is confirmed. The absence of stop codon has not been observed for the gene of other mammalian proteins. The cDNA (thus the mRNA) of napsin A is present in different human tissues. It was of interest to see if napsin A gene is capable of expressing protein product. These results are described below.

B. Human Napsin B.

1. cDNA and Gene Structure.

Clones 559204 and 163167 expressing human napsin B were obtained from ATCC and partially sequenced as described above. FIGS. 4A–4E displays the resulting full-length DNA sequence encoding Napsin B (SEQ ID No. 7) and the predicted amino acid sequence (SEQ ID No. 8). Nucleotides 1–1191 were obtained from genomic clones (described above for Napsin A) and from 1192–1910 from ATCC cDNA clones. The napsin B gene sequence is 92% identical to that of napsin A, and the putative protein sequence from each exhibits 91% identity. The deduced napsin B protein sequence (SEQ ID No. 8, FIG. 4) possesses typical aspartic protease motifs, and the same c-terminal extension, RGD motif, and proline-rich regions as in the deduced protein sequence of napsin A (SEQ ID No. 2, FIG. 1). Unlike the napsin A gene, napsin B gene has an in-frame stop codon.

II. Isolation and Characteization of Napsin Protein.

The comparison of the napsin A sequence with one other and one mouse aspartic protease proenzymes is shown in FIGS. 2A–2C. It is clear that napsin is related to human cathepsin D, and is similar to mouse aspartic protease-like protein, but the differences are readily apparent. The relationship to other human aspartic proteases is further analyzed in FIG. 2D, which is a diagram of degree of relatedness and also presents the percentage of identical residues. Clearly, by both criteria, napsin differs as much from other aspartic proteases as they differ from one another.

In addition to the sequence similarity to the other human aspartic proteases, the conclusion that napsin is an aspartic protease is drawn from the following observations. (a) The critical active site aspartic residues at positions 32 and 215 are present in the conversed DTG sequences. (b) The presence of Tyr-75 (Y) and some conserved residues around it indicate a functional 'flap' which is characteristic of aspartic proteases. (c) The pro region corresponding to residues 1p to 44p is present in napsin, indicating that it is a proenzyme of the aspartic protease and is capable of activation.

An RGD sequence is found at position 315 to 317 (porcine pepsin residue numbers by convention). This motif has been shown to be important in integrin bonding which is related to the regulation of cellular functions such as cell cycle, hemostasis, inflammation and cell proliferation. This sequence may have particular functional meaning for napsin.

2. Immunochemical Detection of Napsin A.

A napsin-specific polyclonal antiserum was produced using the following procedure. An 18 amino acid epitope of Napsin A which was synthesized as a multiple antignic peptide (MAP) on a poly-lysine backbone by the Molecular Biolgy Resource Facility (OUHSC). This epitope (MKSGARVGLARARPRG) (Met Lys Ser Gly Ala Arg Val Gly Leu Ala Arg Ala Arg Pro Arg Gly; amino acids 390 to 405 of SEQ ID No. 2) was common to both napsin A and B, and sufficiently dissimilar from cathepsin D, their closest homolog. This region is likely to be located on the surface of Napsin A as determined from the cathepsin D crystal structure coordinates (Erickson, 1993). Aliquots of 1 mg in 1 ml of $H_2O$ were used to immunize goats (Hybridoma Lab, Oklahoma Medical Research Foundation). Serum collected was ammonium sulfate precipated multiple times (Antibodies Lab manual) and affinity purified using the Napsin A MAP coupled to affi-gel 10 (BioRad). This anti sera was used at 1:5000 dilution in the detection of Napsin A on PVDF membranes transblotted from SDS-PAGE gels (NOVEX). The ECL system (Pierce) was used for detection of primary antibody.

Immunoblots of recombinant Napsin A sample from human kidney 293 cells prepared as described above detected Napsin A. These results show expression of napsin A gene produced an immunospecific band which migrated in SDS-polyacrylamide electrophoresis with a similar mobility to that of napsin B. Thus, despite of the absence of a stop codon in napsin A, its protein is correctly expressed in a human cell line. The fact that this napsin A protein was recovered from the pepstatin-affinity column suggests that the presence of an active site similar to all aspartic proteases.

3. Detection of Napsin B in Human Tissue and Cell Lines

Sections of approximately 8 grams of human kidney cortex (Cooperative Human Tissue Network, National Cancer Institute, NIH) were homogenized in a Waring blender in buffer composed of 20 mM Tris HCl, 50 mM NaCl, 20 mM zwittergent, and 1 μM each of TPCK, TLCK, and EDTA, pH 7.5 (buffer TZ). The homogenate was made 40% ammonium sulfate with gentle stirring, and centrifuged 10,000 ×g. The resulting supernatant was made 70% ammonium sulfate and centrifuged 10,000 ×g. The material insoluble in 70% ammonium sulfate (the 40–70% cut) was dissolved in 15 ml of buffer TZ and made pH 4.0 with 30 ml of NAZ buffer. Following incubation on ice for 1 hour, the sample was centrifuged at 14,000 ×g. To the resulting supernatant, a 0.1 ml aliquot of pepstatin-A-agarose (Sigma) was added. Detection of napsin B in cell lines followed the procedure outlined above for detection of recombinant napsin A.

Napsin B was detected in tissue samples of human kidney cortex and in the human kidney cell line Hut-78: human kidney (0–40% ammonium sulfate cut); human kidney (40–70% cut); Hut-78 cells, in apparently four forms. In the 0–40% ammonium sulfate cut, a single-chain protease of 50–54 kDa with a heterogeneous amino terminus sequence derived from the protein sequence of SPGDKPIFVPLSNYR Ser Pro Gly Asp Lys Pro Ile Phe Val Pro Leu Ser Asn Tyr Arg (amino acids 60 to 74 of SEQ ID No. 8) (with other termini at Asp4 and Lys5) was detected. These N-terminal sequences agreed well with the predicted activation cleavage site in pronapsin B by comparing to the activation cleavage sites in homologous procathepsin D and other aspartic protease zymogens. In the 40–70% ammonium sulfate cut, three forms were detected. A 45–50 kDa single chain form, and two two-chain forms. The 46–50 kDa band produced the same heterogeneous sequence Napsin B sequence as obtained for the larger molecular weight band in the 40% ammonium sulfate cut. The two lower molecular weight fragments of approximately 8 and 4 kDa produced the same amino-terminal sequence (VRLCLSGFQALDVPPPAGPF) (Val Arg Leu Cys Leu Ser Gly Phe Gln Ala Leu Asp Val Pro Pro Pro Ala Gly Pro Phe; amino acids 351 to 370 of SEQ ID No. 8) corresponding to the C-terimal region of Napsin B. A prominent 40 kDa band of the transblotted preparation was sequenced, and produced the same heterogeneous amino terminal sequence as the 46–50 kDa band, indicating two species of two-chain Napsin B: an 8 kDa and 40 kDa as well as a 4 kDa and a 40 kDa species.

III. Applications of Napsin.

A variety of clinical and diagnostic uses for the enzyme can be designed based on analogy to the uses of the related aspartic proteases. The proteins, nucleotide molecules, and methods for isolation and use thereof have a wide variety of applications, particularly in diagnostic applications. Since aspartic proteases are well known to be correlated with certain disorders, such as breast cancer and high blood pressure, and napsin is expressed in the kidney, measurement of the levels and/or types of napsin expressed in tissue, especially kidney, can be correlated with the presence and severity of disorders. The recombinant DNA and reagents derived thereform can be used to assay for napsin expression in healthy and in people inflicted with illness. Napsin sequences can be used to track the presence of napsin genes in patients for possible linkage to diseases.

A. Diagnostic Applications

The amount of napsin can be determined using standard screening techniques, ranging from isolation of napsin from the tissue, using for example immobilized anti-napsin (or anti-napsin A or anti-napsin B) or pepstatin, to detection and quantification with labelled antibodies, to determination of the amount of mRNA transcribed in the tissue, using labelled nucleotide probes.

Antibody Production

Polyclonal antibodies were produced using standard techniques for immunization of an animal with purified protein in combination with an adjuvant such as Freunds' adjuvant. Monoclonal antibodies can also be prepared using standard techniques, for example, by immunizing mice until the antibody titer is sufficiently high, isolating the spleen and doing a fusion, and then screening the hybridomas for those producing the antibodies of interest. These can be antibodies reactive with any napsin, or reactive with napsin A but not B and vice versa.

Humanized antibodies for therapeutic applications, and recombinant antibody fragments can also be generated using standard methodology. A humanized antibody is one in which only the antigen-recognition sites or complementarity-determining hypervariable regions (CDRs) are of non-human origin, and all framework regions (FR) of variable domains are products of human genes. In one method of humanization of an animal monoclonal anti-idiotypic antibody, RPAS is combined with the CDR grafting method described by Daugherty et al., *Nucl. Acids Res.*, 19:2471–2476 (1991). Briefly, the variable region DNA of a selected animal recombinant anti-idiotypic ScFv is sequenced by the method of Clackson, T., et al., *Nature*, 352:624–688 (1991). Using this sequence, animal CDRs are distinguished from animal framework regions (FR) based on locations of the CDRs in known sequences of animal variable genes. Kabat, H. A., et al., Sequences of Proteins of Immunological Interest, 4th Ed. (U.S. Dept. Health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection. The expression of recombinant CDR-grafted immunoglobulin gene is accomplished by its transfection into human 293 cells (transformed primary embryonic kidney cells, commercially available from American Type Culture Collection, Rockville, Md. 20852) which secrete fully grafted antibody. See, e.g., Daugherty, B. L., et al., *Nucl. Acids Res.*, 19:2471–2476, 1991. Alternatively, humanized ScFv is expressed on the surface of bacteriophage and produced in *E. coli* as in the RPAS method described below.

Pharmacia's (Pharmacia LKB Biotechnology, Sweden) "Recombinant Phage Antibody System" (RPAS) may be used for this purpose. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Using the antigen-driven screening system, the ScFv with binding characteristics equivalent to those of the original monoclonal antibody is selected [See, e.g., McCafferty, J., et al., *Nature*, 348:552–554 (1990); Clackson, T., et al., *Nature*, 352:624–688 (1991). The recombinant ScFv includes a considerably smaller number of epitopes than the intact monoclonal antibody, and thereby represents a much weaker immunogenic stimulus when injected into humans. An intravenous injection of ScFv into humans is, therefore, expected to be more efficient and immunologically tolerable in comparison with currently used whole monoclonal antibodies [Norman, D. J., et al., *Transplant Proc.*, 25, suppl. 1:89–93 (1993).

Nucleotide Probes

Nucleotide probes can be used to screen for napsin expression or the types and/or ratios of isoforms present. These can be cDNA sequences or other molecules designed based on the sequences reported herein, or which are obtained using standard techniques from libraries generated from different cell types or species. It is understood that while the sequence reported here is of human origin, the same proteases will be present in other species of animals, and will vary to some degree in both the amino acid sequence and the nucleotide sequence. Napsin is referred to herein as an aspartic protease having the naturally occuring amino acid sequence from human or other animals, or a composite sequence constructed by substitution of amino acids from one species into another, at the equivalent position, other than at the active site, discussed above. A nucleotide molecule encoding napsin can be naturally occurring, as described herein, or designed and made synthetically based on the amino acid sequence. Moreover, since at least two isoforms have been identified, it is expected that additional isoforms will be found in tissues other than kidney or liver. These isoforms are intended to encompassed within the term "napsin".

Nucleotide molecules can be used to assay for amount, type or a combination thereof, using standard diagnostic techniques. In general, probes will include a segment from a DNA encoding napsin of at least fourteen nucleotides, which should be sufficient to provide specificity under standard hybridization conditions, and even more so under stringent conditions. Reaction conditions for hybridization of an oligonucleotide probe or primer to a nucleic acid sequence vary from oligonucleotide to oligonucleotide, depending on factors such as oligonucleotide length, the number of G and C nucleotides, and the composition of the buffer utilized in the hybridization reaction. Moderately stringent hybridization conditions are generally understood by those skilled in the art as conditions approximately 25° C. below the melting temperature of a perfectly base-paired double-stranded DNA. Higher specificity is generally achieved by employing incubation conditions having higher temperatures, in other words more stringent conditions. In general, the longer the sequence or higher the G and C content, the higher the temperature and/or salt concentration required. Chapter 11 of the laboratory manual of Sambrook et al., MOLECULAR CLONING: A LABORATORY MANUAL, second edition, Cold Spring Harbor Laboratory Press, New York (1990), describes hybridization conditions for oligonucleotide probes and primers in great detail, including a description of the factors involved and the level of stringency necessary to guarantee hybridization with specificity. Below 10 nucleotides, hybridized systems are not stable and will begin to denature above 20° C. Above 100,000 nucleotides, one finds that hybridization (renaturation) becomes a much slower and incomplete process, as described in greater detail in the text MOLECULAR GENETICS, Stent, G. S. and R. Calender, pp. 213–219 (1971). Ideally, the probe should be from 20 to 10,000 nucleotides. Smaller nucleotide sequences (20–100) lend themselves to production by automated organic synthetic techniques. Sequences from 100–10,000 nucleotides can be obtained from appropriate restriction endonuclease treatments. The labeling of the smaller probes with the relatively bully chemiluminescent moieties may in some cases interfere with the hybridization process.

Labels

Both antibodies and nucleotide molecules can be labelled with standard techniques, for example, with radiolabels, fluorescent labels, chemiluminescent labels, dyes, enzymes, and other means for detection, such as magnetic particles. For example, selective labeling of the active site with fluorescein can be performed by the method of Bock (Bock, P. E. (1988) *Biochemistry* 27, 6633–6639). In brief, a blocking agent is reacted with enzyme for 1 hour at room temperature. After dialysis, the covalently modified enzyme is incubated at room temperature for one hour with 200 μM 5-(iodoacetamido)fluorescein (Molecular Probes). Free fluorescein is removed by gel filtration on a PD-10 column (Pharmacia). With this method, each molecule of fluorescinated enzyme contains a single dye at the active site and hence all of the fluorescent molecules behave identically. Alternatively, iodogen (Pierce) can be used to radiolabel enzyme with Na[$^{125}$I] (Amersham) according to the manufacture's protocol. Free $^{125}$I can be removed by gel filtration on a PD-10 column.

Recombinant Protein

Recombinant proteins, and fragments thereof, are useful as controls in diagnostic methods. The cDNA and gene sequences of napsin A were determined. The DNA was expressed in a recombinant system (human cell line) and the activity of the enzyme characterized. The cDNA and gene sequences of napsin B were determined. The proteins can be used as standards, or as discussed below, therapeutically as aspartic proteases and in studies of enzyme behavior. The expression of recombinant proteins from a cDNA without stop codon may offer certain advantages.

Procedures for Isolation of Napsin

Antibodies and nucleotide probes are primarily useful in the detection of napsin, or its isoforms. In some cases it may also be useful to isolate the purified protein. As described above, a procedure was devised to bind napsin A and napsin B on to a pepstatin-affinity column. Immobilized pepstatin can be used to purify either naturally occurring, or recombinant, napsin, from tissues in which it is expressed, for diagnostic applications.

B. Enzyme Applications.

The aspartic proteases may be useful in applications similar to those for which cathepsin D are used. Clinically, it may be advantageous to transfect, even transiently, the gene encoding napsin to treat disorders in which the individual is deficient in the protease, or to transfect an antisense, targeted ribozyme or ribozyme guide sequence, or triple helix to prevent or decrease enzyme expression, in individuals with disorders characterized by elevated levels of enzyme.

Modifications and variations of the present invention will be obvious to those skilled in the art and are intended to come within the scope of the following claims.

We claim:

1. An isolated napsin containing a C-tenninal extension and a plurality of proline residues comprising the amino acid sequence of amino acids 390 to 405 of SEQ ID No. 2 and having greater than 47% identical amino acid residues with SEO ID No. 2, wherein the Napsin is capable of functioning as an aspartic protease, and wherein the napsin is encoded by a nucleotide molecule hybridizing under stringent conditions to a nucleotide molecule encoding the amino acid sequence of SEQ ID No. 2 or 4.

2. The napsin of claim 1 wherein the protein is isoform A and has at least 91% homology to SEQ ID No. 2.

3. The napsin of claim 2 consisting of the amino acid sequence of SEQ ID No. 2.

4. The napsin of claim 2 encoded by SEQ ID No. 1.

5. The napsin of claim 1 wherein the protein is isoform B and has at least 91% homology to SEQ ID No. 8.

6. The napsin of claim 5 consisting of the amino acid sequence of SEQ ID No. 4.

7. The napsin of claim 5 encoded by SEQ ID No. 7.

8. The napsin of claim 2 containing a C-terminal extension wherein the Napsin contains Napsin contains a Cysteine residue at a position equivalent to position 354 of SEQ ID. No. 2.

9. The napsin of claim 1 containing an RGD motif wherein the Napsin is capable of functioning as an aspartic protease.

10. The napsin of claim 5 containing an RGD motif and a C-terminal extension wherein the Napsin is capable of functioning as an aspartic protease.

11. The isolated Napsin of claim 10 further comprising aproline-rich region.

* * * * *

UNITED STATES PATENT AND TRADEMARK OFFICE
CERTIFICATE OF CORRECTION

| | |
|---|---|
| PATENT NO. | : 6,225,103 B1 |
| APPLICATION NO. | : 08/974691 |
| DATED | : May 1, 2001 |
| INVENTOR(S) | : Gerald Koelsch et al. |

Page 1 of 1

It is certified that error appears in the above-identified patent and that said Letters Patent is hereby corrected as shown below:

On Title page in the Inventors Item (75), please replace "Gerald Keolsch" with --Gerald Koelsch--.

Signed and Sealed this

Fourth Day of November, 2008

JON W. DUDAS
*Director of the United States Patent and Trademark Office*